United States Patent [19]

Ferrini et al.

[11] 4,192,873
[45] Mar. 11, 1980

[54] ANTI-INFLAMMATORY 2-SULPHONYL- (OR -SULPHINYL)-2-AMINOACETOPHENONES

[75] Inventors: Pier G. Ferrini, Binningen; Richard Göschke; Alfred Sallmann, both of Bottmingen; Alberto Rossi, Oberwil, all of Switzerland

[73] Assignee: Ciba-Geigy Corporation, Ardsley, N.Y.

[21] Appl. No.: 846,305

[22] Filed: Oct. 28, 1977

[30] Foreign Application Priority Data

Nov. 25, 1976 [CH] Switzerland ............... 14845/76

[51] Int. Cl.$^2$ ............... A61K 31/135; A61K 31/44; C07C 87/50; C07C 87/60
[52] U.S. Cl. ............... 424/246; 260/326.82; 260/556 B; 260/571; 260/577; 544/59; 544/158; 544/383; 546/192; 546/334; 424/248.5; 424/248.52; 424/250; 424/267; 424/274; 424/321; 424/330; 424/263
[58] Field of Search ............... 260/556 B, 577, 592, 260/294.8 G, 294.8 R, 571, 326.82; 544/236, 59, 158, 383; 424/263, 321, 330, 248.5, 248.52, 250, 267, 274; 546/192

[56] References Cited

U.S. PATENT DOCUMENTS

| 2,797,218 | 6/1957 | Barber et al. ............... 544/235 |
| 3,355,494 | 11/1967 | Lyness et al. ............... 260/592 X |
| 3,409,674 | 11/1968 | Moore ............... 260/592 |
| 3,637,803 | 1/1972 | Shen et al. ............... 260/592 X |
| 3,937,704 | 2/1976 | Strandtmann et al. ............... 260/578 X |

OTHER PUBLICATIONS

Leonard, N. J., "The Chemistry of Cinnolenes", Chim Rev. 37, only pp. 269, 270, 271 & 272 relied upon.

Primary Examiner—Thomas A. Waltz
Attorney, Agent, or Firm—Theodore O. Groeger

[57] ABSTRACT

The invention relates to novel ortho-aminoacetophenones of the formula I

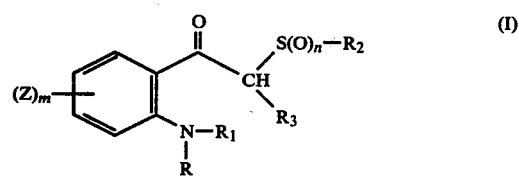

and their tautomers, in which Z is hydrogen, halogen, lower alkyl, cycloalkyl, lower alkoxy, trifluoromethyl, nitro or substituted or unsubstituted sulphamoyl, m is 1 or 2, R is hydrogen, aryl or lower alkyl, $R_1$ is hydrogen or lower alkyl, $R_2$ is lower alkyl, cycloalkyl, aryl, cycloalkyl-lower alkyl, aryl-lower alkyl or substituted or unsubstituted pyridyl, $R_3$ is hydrogen or lower alkyl and n is 1 or 2, with the exception of 2'-[N-(p-methoxyphenyl)-amino]-2-(methyl-sulphinyl)-acetophenone, 2'-amino-2-(methylsulphinyl)-acetophenone, 2'-amino-5'-chloro-2-(methylsulphinyl)-acetophenone, 2'-methylamino-2-(methylsulphinyl)-acetophenone, 2'-amino-5'-methyl-2-(methylsulphinyl)-acetophenone, 2'-amino-4'-chloro-2-(methylsulphinyl)-acetophenone, 2'-amino-6'-chloro-2-(methylsulphinyl)-acetophenone, 2'-amino-5',6'-dimethoxy-2-(methylsulphinyl)-acetophenone and 2'-amino-4',5'-dimethoxy-2-(methylsulphinyl)-acetophenone, and also to their salts.

These compounds have a fibrinolytic and an antiinflammatory action.

13 Claims, No Drawings

ANTI-INFLAMMATORY 2-SULPHONYL- (OR -SULPHINYL)-2-AMINOACETOPHENONES

The invention relates to novel ortho-aminoacetophenones of the formula I

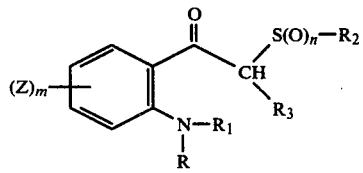

and their tautomers, in which Z is hydrogen, halogen, lower alkyl, cycloalkyl, lower alkoxy, trifluoromethyl, nitro or substituted or unsubstituted sulphamoyl, m is 1 or 2, R is hydrogen, aryl or lower alkyl, $R_1$ is hydrogen or lower alkyl, $R_2$ is lower alkyl, cycloalkyl, aryl, cycloalkyl-lower alkyl, aryl-lower alkyl or substituted or unsubstituted pyridyl, $R_3$ is hydrogen or lower alkyl and n is 1 or 2, with the exception of 2'-[N-(p-methoxyphenyl)-amino]-2-(methyl-sulphinyl)-acetophenone, 2'-amino-2-(methylsulphinyl)-acetophenone, 2'-amino-5'-chloro-2-(methylsulphinyl)-acetophenone, 2'-methylamino-2-(methylsulphinyl)-acetophenone, 2'-amino-5'-methyl-2-(methylsulphinyl)-acetophenone, 2'-amino-4'-chloro-2-(methylsulphinyl)-acetophenone, 2'-amino-6'-chloro-2-(methylsulphinyl)-acetophenone, 2'-amino-5',6'-dimethoxy-2-(methylsulphinyl)-acetophenone and 2'-amino-4',5'-dimethoxy-2-(methylsulphinyl)-acetophenone, and also to their salts and processes for the preparation of these compounds.

In the preceding and following text, a lower radical is understood as meaning, especially, a radical of the said type having up to 7 C atoms and in particular up to 4 C atoms.

Halogen is especially fluorine or bromine and in particular chlorine.

Lower alkyl is, for example, propyl or isopropyl or straight-chain or branched butyl, pentyl, hexyl or heptyl, which are bonded in any position, and in particular methyl and ethyl.

Cycloalkyl has, in particular, 3 to 8 and especially 5–7 ring members and is in particular cyclopropyl, cyclobutyl, cyclopentyl, cyclohexyl, cycloheptyl or cyclooctyl.

Lower alkoxy is, for example, ethoxy, propoxy, isopropoxy or straight-chain or branched butoxy, pentyloxy, hexyloxy or heptyloxy, which are bonded in any position, or in particular methoxy.

Substituted or unsubstituted sulphamoyl is, especially, sulphamoyl, N-lower alkyl-sulphamoyl, N,N-dilower alkylsulphamoyl, N,N-lower alkylene-sulphamoyl having preferably 4–8 ring members, N,N-oxalower alkylene-sulphamoyl having preferably 4 or 5 C atoms in the oxaalkylene chain, N,N-thialower alkylene-sulphamoyl having preferably 4 or 5 C atoms in the thiaalkylene chain, or N,N-aza-lower alkylene-sulphamoyl having preferably 4 or 5 C atoms in the azaalkylene chain. Substituted or unsubstituted sulphamoyl is, accordingly, in particular sulphamoyl, N-methylsulphamoyl, N,N-dimethylsulphamoyl, N,N-diethylsulphamoyl, N-ethylsulphamoyl, N-propylsulphamoyl, N-butylsulphamoyl, pyrrolidinosulphonyl, piperidinosulphonyl, morpholinosulphonyl, thiomorpholinosulphonyl, 2,6-dimethylthiomorpholinosulphonyl, piperazinosulphonyl, N'-methylpiperazinosulphonyl or N'-(β-hydroxyethyl)-piperazinosulphonyl.

Aryl is, for example, phenyl which is polysubstituted or monosubstituted by lower alkoxy, lower alkyl, halogen, trifluoromethyl or nitro, or is unsubstituted phenyl.

Aryl-lower alkyl is, in particular, phenyl-lower alkyl, for example benzyl or α- or β-phenylethyl, in which the phenyl radical can also carry one, two or three substituents, for example lower alkyl radicals, lower alkoxy radicals, halogen atoms, trifluoromethyl groups or nitro groups.

Cycloalkyl-lower alkyl is lower alkyl substituted in any position by cycloalkyl and is especially cyclopropylmethyl, 2-cyclopropylethyl, cyclopentylmethyl, 2-cyclopentylethyl, cyclohexylmethyl or 2-cyclohexylethyl.

Pyridyl is especially 2-pyridyl, 3-pyridyl or 4-pyridyl and can be substituted by lower alkyl, lower alkoxy, halogen or trifluoromethyl, but is preferably unsubstituted.

The novel compounds possess valuable pharmacological properties, in particular a fibrinolytic and an anti-inflammatory action.

Thus, in rats, on oral administration of 1 to 30 mg/kg, they effect a distinct shortening in the euglobulin clot lysis time (Pharmacology, 4, 242, 1970 or Pharmacology, 7, 51–61, 1972).

Furthermore, in the kaolin oedema test on rats, paws they show a distinct anti-inflammatory action on oral administration in a dose of 30 to 300 mg/kg.

The novel compounds can therefore be used as fibrinolytic agents and thrombolytic agents and as antiphlogistic agents. However, they are also valuable intermediates for the preparation of other useful substances, especially of pharmacologically active compounds.

The invention relates in particular to ortho-aminoacetophenones Ia of the formula I, in which Z, m, $R_1$, $R_2$, $R_3$ and n are as defined above and R is aryl.

The invention also relates in particular to ortho-amino-acetophenones Ib of the formula I, in which Z, m, R, $R_1$ and $R_2$ are as defined above and $R_3$ is hydrogen or lower alkyl having 1–3 C atoms, with the exception of the compounds mentioned above by name.

The invention also relates in particular to ortho-amino-acetophenones Ic of the formula I, in which Z is hydrogen, halogen, lower alkyl, cycloalkyl, lower alkoxy, trifluoromethyl or substituted or unsubstituted sulphamoyl, m is 1, R is hydrogen, lower alkyl or phenyl which is unsubstituted or polysubstituted or monosubstituted by lower alkyl, lower alkoxy, halogen or trifluoromethyl, $R_1$ is hydrogen or lower alkyl, $R_2$ is lower alkyl, phenyl which is unsubstituted or polysubstituted or, especially, monosubstituted by lower alkyl, lower alkoxy, halogen or trifluoromethyl, benzyl which is unsubstituted or polysubstituted or, especially, monosubstituted by lower alkyl, lower alkoxy, halogen or trifluoromethyl, or pyridyl, i.e. 2-pyridyl, 3-pyridyl or 4-pyridyl, n is 1 or 2 and $R_3$ is hydrogen or methyl, with the exception of the compounds mentioned above by name.

The invention also relates especially to ortho-aminoacetophenones Id of the formula I, in which m is 1 and Z is hydrogen, lower alkyl, cyclopentyl, cyclohexyl, lower alkoxy, trifluoromethyl or substituted or unsubstituted sulphamoyl, R is lower alkyl or phenyl which is unsubstituted or polysubstituted or monosubstituted by lower alkyl, lower alkoxy, halogen or trifluoromethyl, $R_1$ is hydrogen or α-unbranched lower alkyl, $R_2$ is lower alkyl, benzyl or phenyl which is unsubstituted or polysubstituted or, especially, monosubstituted by lower alkyl, lower alkoxy, halogen or trifluoromethyl, or pyridyl, n is 2 and $R_3$ is hydrogen, with the exception of the compounds mentioned above by name.

The invention also relates especially to ortho-amino-acetophenones Ie of the formula I, in which m is 1 and Z is hydrogen, lower alkyl, cyclopentyl, cyclohexyl, lower alkoxy, trifluoromethyl or sulphamoyl, R is lower alkyl or phenyl which is unsubstituted or polysubstituted or, especially, monosubstituted by lower alkyl, lower alkoxy, halogen or trifluoromethyl, $R_1$ is hydrogen, $R_2$ is lower alkyl, benzyl or phenyl which is unsubstituted or polysubstituted or, especially, monosubstituted by lower alkyl, lower alkoxy, halogen or trifluoromethyl, or 2-pyridyl, 3-pyridyl or 4-pyridyl, $R_3$ is hydrogen and n is 1 or 2, with the exception of the compounds mentioned above by name.

Compounds to be mentioned in particular are also ortho-amino-acetophenones If of the formula I, in which m is 1, Z is 3-, 4- or 6-lower alkyl, 5-($C_{2-7}$)-lower alkyl, cyclopentyl, cyclohexyl, lower alkoxy, trifluoromethyl, 3-halogen, 4-fluoro, 4-bromo, 5-fluoro, 5-bromo, 6-fluoro, 6-bromo or substituted or unsubstituted sulphamoyl, R, $R_1$ and $R_3$ are hydrogen, $R_2$ is methyl and n is 1.

Compounds to be mentioned in particular are also ortho-amino-acetophenones Ig of the formula I, in which m is 2, Z is hydrogen, lower alkyl, lower alkoxy with the exception of 4-, 5- and 6-methoxy, trifluoromethyl, halogen or substituted or unsubstituted sulphamoyl, R and $R_1$ are hydrogen, $R_2$ is methyl, $R_3$ is hydrogen and n is 1.

The invention also relates in particular to ortho-amino-acetophenones Ih of the formula I, in which m is 1 or 2, Z is halogen, lower alkyl, cycloalkyl, lower alkoxy, trifluoromethyl, lower alkyl-sulphamoyl or di-lower alkylsulphamoyl, R is methyl, $R_1$ is hydrogen, $R_2$ is methyl, $R_3$ is hydrogen and n is 1.

The invention also relates especially to ortho-amino-acetophenones Ii of the formula I, in which m is 1 or 2, Z is halogen, lower alkyl, cycloalkyl, lower alkoxy, trifluoromethyl or di-lower alkyl-sulphamoyl, R is p-methoxyphenyl, $R_1$ is hydrogen, $R_2$ is methyl, $R_3$ is hydrogen and n is 1.

With the exception of the compounds mentioned above by name, compounds to be mentioned very particularly are: ortho-amino-acetophenones Ij of the formula I, in which Z is hydrogen, halogen or di-lower alkyl-sulphamoyl, m is 1 or 2, R is hydrogen, phenyl, trifluoromethylphenyl, bis-trifluoromethylphenyl, lower alkylphenyl, di-lower alkylphenyl, halogenophenyl, dihalogenophenyl, halogeno-lower alkylphenyl or lower alkyl, $R_1$ is hydrogen or lower alkyl, $R_2$ is lower alkyl or phenyl, $R_3$ is hydrogen and n is 1 or 2, and especially in which Z is hydrogen, chlorine or dimethylsulphamoyl, m is 1, R is hydrogen, 3,5-bis-trifluoromethylphenyl, 3-trifluoromethylphenyl, 2,6-dichlorophenyl, 2-methyl-3-chloro-phenyl, 2,3-dimethylphenyl or methyl, $R_1$ is hydrogen or methyl, $R_2$ is methyl or phenyl, $R_3$ is hydrogen and n is 1 or 2, and very particularly the compounds mentioned in the examples.

The novel compounds can be obtained by methods which are known per se.

The novel compounds of the formula I can be obtained, for example, by reacting an isatoic anhydride, which is unsubstituted or substituted by the group $(Z)_m$ and/or the group R or $R_1$, or a compound of the formula II

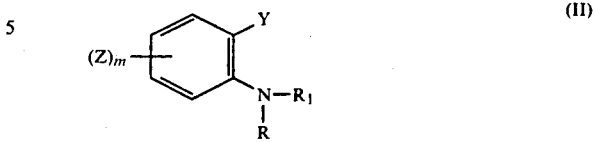

in which Z, m, R and $R_1$ are as defined above and Y is a reactive, functionally modified carboxyl group, with a compound of the formula III

in which $M^\oplus$ is an alkali metal cation and n, $R_2$ and $R_3$ are as defined above.

An alkali metal cation is especially a sodium or lithium cation.

A reactive, functionally modified carboxyl group is, for example, a group $-COR_x$, in which $R_x$ is a halogen atom, an azido group or, together with the carbonyl group, an anhydride group, or preferably an etherified hydroxyl group.

An etherified hydroxyl group is, especially, a lower alkoxy group in which the lower alkyl part preferably has up to 7 C atoms and can be straight-chain or branched.

Halogen is fluorine, bromine, iodine or, in particular, chlorine.

Anhydride groups are preferably mixed anhydride groups in which the part $R_x^\ominus$, which leaves during cyclisation, is preferably a lower alkyl-carboxylate anion or a lower alkoxycarboxylate anion.

The reaction can be carried out in a conventional manner, preferably in a polar solvent, for example dimethylsulphoxide, dioxane or tetrahydrofurane, and at room temperature or elevated temperature, or preferably at reduced temperature. The condensation reaction can be carried out under a nitrogen atmosphere if necessary.

When isatoic anhydride, which is unsubstituted or substituted by the group $(Z)_m$ and/or the group R or $R_1$, is used, the desired compound of the formula I is obtained after spontaneous decarboxylation of the carbamic acid formed as an intermediate.

Furthermore, a compound of the formula IV

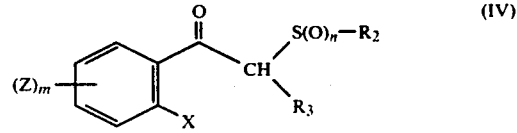

in which X is a nucleophilically detachable group and Z, m, $R_2$, $R_3$ and n are as defined above, can be reacted with a compound of the formula V

in which R is substituted or unsubstituted phenyl and $R_1$ is lower alkyl or preferably hydrogen.

A nucleophilically detachable group X is preferably a halogen atom, for example a chlorine or iodine atom or especially a bromine atom, or an ammonium group, such as a tri-lower alkyl-ammonium group, for example the trimethylammonium group, or a lower alkylsulphonyl group, for example the methylsulphonyl group.

The reaction is preferably carried out in a high-boiling polar solvent, for example n-amyl alcohol, dimethylformamide or nitrobenzene, in the presence of a basic condensing agent, such as an alkali metal carbonate, for example potassium carbonate, and preferably in the presence of a catalyst which accelerates the reaction, for example metallic copper. The reaction is preferably carried out at elevated temperature, for example at the reflux temperature of the corresponding solvent.

Furthermore, in order to prepare compounds of the formula I in which $R_1$ is hydrogen, the group A in a compound of the formula VI

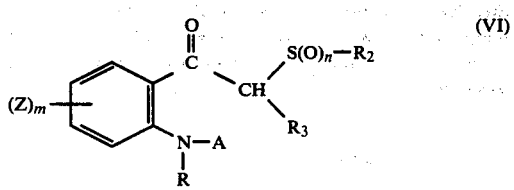

in which Z, m, R, $R_2$, $R_3$ and n are as defined above and A is an acyl group, can be detached hydrolytically.

The acyl group A is a lower alkanoyl group, but preferably an aroyl group.

A lower alkanoyl group is, for example, the formyl, acetyl, propionyl or butyryl group.

An aroyl group is, for example, the benzoyl group or a substituted benzoyl group. A substituted benzoyl group carries as substituents preferably halogen, nitro, lower alkyl, trifluoromethyl and/or lower alkoxy groups.

The hydrolysis can be carried out in a conventional manner. A reaction medium which can be used is either an acid reaction medium (preferably when n is 2) or, preferably, a basic reaction medium. When a basic reaction medium is used, the compound of the formula VI is dissolved, for example, in a water-soluble organic solvent, such as a lower alkanol, for example methanol or ethanol, and a large excess of concentrated alkali metal hydroxide solution, especially sodium hydroxide solution or potassium hydroxide solution, is added. The reaction is preferably carried out at elevated temperature, for example at the reflux temperature of the reaction mixture.

Furthermore, in a compound of the formula VII

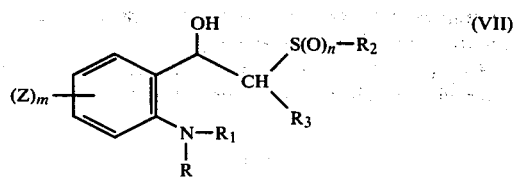

in which Z, m, R, $R_1$, $R_2$, $R_3$ and n are as defined above, the secondary hydroxyl group can be oxidised to a carbonyl group.

Oxidising agents which can be used are the customary alcohol oxidising agents, for example oxygen (if desired in the presence of a suitable catalyst, for example copper) or chromium-VI oxide, but preferably active manganese dioxide.

When active manganese dioxide is used, the reaction is preferably carried out in an inert organic solvent, such as carbonyl compounds, for example acetone or cyclohexanone or halogenated or non-halogenated hydrocarbons, for example benzene, hexane, chloroform or methylene chloride, or lower alkanecarboxylic acid nitriles, for example acetonitrile, at elevated or reduced temperature, but preferably at room temperature.

When compounds of the formula VII in which n is 1 are oxidised by oxidising agents other than manganese dioxide, care must be taken, if necessary, to ensure that the sulphinyl group is not oxidised to the sulphonyl group.

Furthermore, a compound of the formula VIII

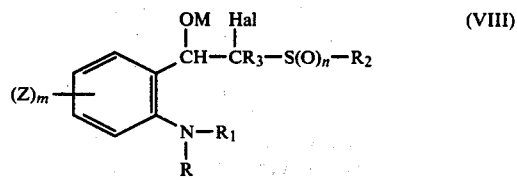

in which Z, m, $R_2$ and $R_3$ are as defined above, R is aryl or lower alkyl, $R_1$ is lower alkyl, n is 1, M is an alkali metal atom, especially a lithium atom, and Hal is a halogen atom, especially a chlorine atom, can be reacted with a compound of the formula IX

$$M-Alk \qquad (IX)$$

in which M is an alkali metal atom, especially a lithium atom, and Alk is lower alkyl, especially methyl, to give compounds of the formula I.

The reaction is preferably effected by adding the compound IX to a solution of the compound VIII in an inert solvent, such as cyclic ethers, for example dioxane or tetrahydrofurane. The reaction temperature chosen is room temperature or, preferably, a reduced temperature, for example 0°.

In resulting compounds of the formula I, substituents can be introduced, modified or detached in the customary manner, within the scope of the end products.

Thus, for example, in resulting compounds in which n is 1, the sulphinyl group can be converted into a sulphonyl group by oxidation. The oxidation is effected with one of the customary S-oxidising agents, such as peracids, for example peracetic acid, or hydrogen peroxide; however, the reaction is preferably carried out using the system hydrogen peroxide/glacial acetic acid.

In resulting compounds of the formula I in which R and/or $R_1$ is hydrogen, the latter can be replaced by the further substituents indicated for R and/or $R_1$. The radical R and/or $R_1$ can be introduced in a conventional manner, for example by reacting the compound I in which R and/or $R_1$ is hydrogen with the equimolar amount or twice the molar amount of a compound RQ or $R_1Q$, in which R and, respectively, $R_1$ have the other meanings indicated above and Q is a reactive esterified hydroxyl group. A reactive esterified hydroxyl group is, especially, a hydroxyl group esterified by a strong inorganic or organic acid, in particular a hydrogen halide acid, such as hydrochloric acid, hydrobromic acid or hydriodic acid, and also sulphuric acid, or a strong organic sulphonic acid, for example benzenesulphonic acid, methanesulphonic acid or 4-toluenesulphonic acid. Thus, Q is especially chlorine, bromine or iodine. This reaction is carried out in the customary manner, preferably in the presence of a basic condensing agent and/or with an excess of the ortho-aminoacetophenone compound. Suitable basic condensing agents are, for example, alkali metal hydroxides, such as sodium hydroxide or potassium hydroxide, alkali metal carbonates, such as potassium carbonate, and alkali metal alcoholates, for example alkali metal lower alkanolates, such as sodium methylate, potassium ethylate and potassium tertiary butylate. The reaction can take place at room temperature or at elevated temperature.

In resulting compounds of the formula I in which $R_3$ is hydrogen, this can be replaced by lower alkyl. The reaction is effected in a conventional manner, for example by reacting the compound of the formula I, which is to be alkylated, together with the alkylating agent, for example a compound of the formula $R_3Z_2$, in which $R_3$ is as defined above and $Z_2$ is a reactive esterified hydroxyl group. $R_3Z_2$ is preferably $R_3Hal$, in which Hal is halogen and especially iodine. The reaction is preferably carried out in a 2-phase system by initially introducing the reactants in a water-insoluble solvent, such as a halogenated hydrocarbon, for example methylene chloride or chloroform, and then adding a dilute aqueous solution of a basic condensing agent, such as an alkali metal hydroxide, for example sodium hydroxide or potassium hydroxide, together with the salt of a tertiary amine, for example with tetrabutylammonium hydrogen sulphate. The reaction is carried out at room temperature or reduced temperature. After the reaction, the alkylated compound of the formula I is in the organic phase. However, the reaction can also be carried out in an aqueous medium, analogously to the procedure described above. In the latter case, the reaction product can then be obtained by extraction with an organic solvent, such as a halogenated hydrocarbon, for example methylene chloride or chloroform.

Depending on the process conditions and the starting materials, the compounds of the formula I are obtained in the free form or in the form of their salts with bases, which is also included in the invention. Resulting free compounds can be converted in a conventional manner into the salts with bases, in particular into therapeutically usable salts with bases, for example salts with organic amines, or metal salts. Possible metal salts are, in particular, alkali metal salts or alkaline earth metal salts, such as sodium salts, potassium salts, magnesium salts or calcium salts. Because of the close relationships between the novel compounds in the free form and in the form of their salts, the free compounds, in the preceding and following text, are, where appropriate, also to be understood to include the corresponding salts in respect of general sense and intended use.

The invention also relates to those embodiments of the process for the preparation of the compounds of the formula I in which a compound obtainable as an intermediate at any stage of the process is used as the starting material and the missing process steps are carried out, or the process is discontinued at any stage, or in which a starting material is formed under the reaction conditions, or in which a reactant can be in the form of its salts and/or its racemate or a mixture of enantimers, or in the form of its antipodes.

The starting materials for compounds of the formula I are known or can be prepared according to known processes.

Thus, for example, compounds of the formula III can be prepared by reacting a compound of the formula $CH_2R_3—S(O)_n—R_2$, in which n, $R_2$ and $R_3$ are as defined above, with an alkali metal hydride, for example sodium hydride, in an inert solvent, for example dimethylsulphoxide, dioxane or tetrahydrofurane, or, if desired, without a solvent, preferably under a nitrogen atmosphere. The solution containing the reagent of the formula III is preferably employed direct as such for the preparation of the compounds according to the invention. In order to determine the content of the active reagent, the solution can be titrated with formanilide and triphenylmethane as the indicator.

Compounds of the formula VI can be prepared, for example, as follows:

Starting from an amine of the formula HN(A)(R), in which R and A are as defined above, the corresponding halogenoimide compound is obtained using a halogenating agent, for example phosphorus pentachloride, and this halogenoimide compound can be converted by reaction with a metal salt of a salicylate, for example the sodium salt of methyl salicylate, into a compound of the formula X

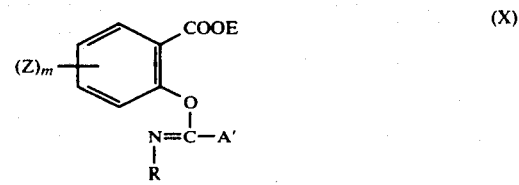

in which R is as defined above,

is A and —COOE is an ester grouping, preferably a lower alkoxycarbonyl group. A rearrangement reaction (Chapman reaction), which is preferably carried out at elevated temperature, gives compounds of the following structure XI

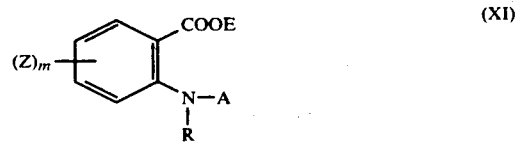

in which R, A and —COOE are as defined above. Compounds of the formula XI can be converted by reaction with compounds of the formula III, as described for compounds of the formula II, into the desired starting compounds of the formula VI.

Compounds of the formula VII can be prepared, for example, as follows: an aldehyde of the formula XII

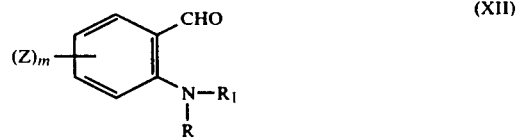

in which R and $R_1$ are as defined above, is treated, under the customary conditions, with a compound of the formula III, a condensation reaction taking place to give compounds of the formula VII.

Compounds of the formula VIII can be synthesised, for example, by the following route: a compound of the formula XIII

$$Hal-CH_2-S(O)_n-R_2 \qquad (XIII)$$

in which $R_2$ is as defined above, n is 1 and Hal is halogen, and halogen is especially chlorine, is metallised, especially with lithium, in the conventional manner to give compounds of the formula XIV.

$$R_2-S(O)_n-\overset{\ominus}{\underset{M^\oplus}{C}H}-Hal \qquad (XIV)$$

The desired starting compounds of the formula VIII are obtained by reacting compounds of the formula XIV with an aldehyde of the formula XII, preferably at reduced temperature and in a suitable solvent, such as a cyclic ether, for example tetrahydrofurane.

Depending on the choice of the starting materials and procedures, the novel compounds of the formula I can be in the form of optical antipodes or racemates or, if they contain at least two asymmetric carbon atoms, also in the form of a mixture of diastereoisomers.

Resulting mixtures of diastereoisomers can be separated in a known manner into the two mixtures of enantiomers on the basis of the physico-chemical differences between the constituents, for example by chromatography and/or fractional crystallisation.

Resulting racemates can be resolved into the diastereomers by known methods, for example by recrystallisation from an optically active solvent or with the aid of microorganisms, and the antipodes can be set free from the diastereomers by the action of suitable agents.

The novel compounds of the formula I can be used as medicines, for example in the form of pharmaceutical formulations which contain the compounds as a mixture with a pharmaceutical, organic or inorganic, solid or liquid excipient suitable, for example, for enteral, for example oral, or parenteral administration. Substances which can be used as excipients are those which do not react with the novel compounds, for example water, gelatine, lactose, starch, magnesium stearate, talc, vegetable oils, benzyl alcohols, polyalkylene glycols, white petroleum jelly, cholesterol or other known medicinal excipients. The pharmaceutical formulations can be in the form of, for example, tablets, dragées, capsules, suppositories, ointments or a cream or in the liquid form as solutions (for example in the form of an elixir or syrup), suspensions or emulsions. They can be sterilised and/or contain auxiliaries, such as preservatives, stabilisers, wetting agents or emulsifiers, salts for changing the osmotic pressure or buffers. The formulations, which can also be used in veterinary medicine, are obtained by conventional methods.

In the case of a warm-blooded animal having a body weight of about 75 kg, the maximum daily dose is about 500 mg administered perorally.

The examples which follow illustrate the invention without, however, restricting it. The temperatures are given in degrees centigrade.

EXAMPLE 1

Under nitrogen, 28.8 g of a 55% strength dispersion of sodium hydride are washed with pentane and then suspended in 180 ml of dimethylsulphoxide. After adding 62 g of dimethylsulphone, the mixture is warmed to 70° (vigorous evolution of gas). After the evolution of hydrogen has ceased, the mixture is cooled to 0°–10°. A solution of 58 g of methyl N-(m-trifluoromethylphenyl)-anthranilate in 200 ml of absolute tetrahydrofurane is added dropwise at this temperature in the course of about 45 minutes. The mixture is stirred for 1 hour at room temperature and is then poured into 3.5 l of ice-water. After acidifying with 2 N hydrochloric acid, the mixture is stirred for a further 2 hours. The crystalline precipitate is filtered off with suction and dissolved in 400 ml of methylene chloride and 100 ml of methanol and the solution is then filtered through Hyflo. After concentrating the solution, a further 100 ml of methanol are added and the solution is then left to stand at 0°. Yellow 2'-[N-(m-trifluoromethylphenyl)-amino]-2-(methylsulphonyl)-acetophenone with a melting point of 121°–123° crystallises out.

EXAMPLE 2

The following compounds can also be obtained in a manner analogous to that described in Example 1:

(a) 2'-[N-methyl-N-(m-trifluoromethylphenyl)-amino]-2-(methylsulphonyl)-acetophenone with a melting point of 85°–86° from methyl N-methyl-N-(m-trifluoromethylphenyl)-anthranilate (boiling point 125°/0.01 mm Hg).

(b) 2'-[N-(m-bis-Trifluoromethylphenyl)-amino]-2-(methylsulphonyl)-acetophenone with a melting point of 156°–157° from methyl N-(m-bis-trifluoromethylphenyl)-anthranilate (boiling point 128°–129°/0.2 mm Hg).

(c) 2'-[N-Methyl-N-(m-bis-trifluoromethylphenyl)-amino]-2-(methylsulphonyl)-acetophenone with a melting point of 105°–107° from methyl N-methyl-N-(m-bis-trifluoromethylphenyl)-anthranilate (boiling point 113°–114°/0.18 mm Hg).

(d) 2'-[N-(2-Methyl-3-chloro-phenyl)-anilino]-2-(methylsulphonyl)-acetophenone with a melting point of 130°–132° from methyl N-(2-methyl-3-chloro-phenyl)-anthranilate (melting point 78°–80°).

EXAMPLE 3

Under nitrogen, 3 g of a 55% strength dispersion of sodium hydride, which has been washed with pentane, are suspended in 30 ml of dimethylsulphoxide. After adding 9.3 g of methylphenylsulphone, the mixture is warmed to 60°. After the evolution of hydrogen has ceased, the mixture is cooled to 0°, diluted with 50 ml of tetrahydrofurane and, at this temperature, a solution of 4 g of methyl N-methyl-5-chloro-anthranilate in 20 ml of tetrahydrofurane is added dropwise in the course of about 20 minutes. The mixture is stirred overnight at room temperature and then poured into about 200 ml of ice-water. The resulting mixture is acidified with 2 N hydrochloric acid and stirred for a further 1 hour. The oily precipitate crystallises slowly. It is filtered off with suction and recrystallised from chloroform/ethanol. 2'-N-Methylamino-5'-chloro-2-(phenylsulphonyl)-acetophenone with a melting point of 160°–162° is obtained.

EXAMPLE 4

Under nitrogen, 17.2 g of a 55% strength dispersion of sodium hydride are suspended in 130 ml of dimethylsulphoxide and the mixture is then slowly warmed to 70°–75°. After the evolution of hydrogen has ceased, the mixture is cooled to 30°–35° and, at this temperature, a solution of methyl N-(2,3-dimethylphenyl)-anthranilate (melting point 92°–94°) in 200 ml of tetrahydrofurane is added dropwise in the course of about 35 minutes. The mixture is stirred for a further 3½ hours at room temperature and is then poured onto 2.5 kg of ice. After acidifying the mixture with concentrated hydrochloric acid, the dark precipitate is filtered off with suction and dissolved in chloroform. This solution is chromatographed on silica gel. The 2'-[N-(2,3-Dimethylphenyl)-amino]-2-(methylsulphinyl)-acetophenone which is eluted is recrystallised from isopropanol. Melting point 110°–112°.

EXAMPLE 5

The following compounds can also be obtained in a manner analogous to that described in Example 4:

(a) 2'-[N-(m-bis-trifluoromethylphenyl)-amino]-2-(methylsulphinyl)-acetophenone with a melting point of 127°–129° from methyl N-(m-bis-trifluoromethylphenyl)-anthranilate (boiling point 130°–132°/0.05 mm Hg), (b) 2'-[N-(o-dichlorophenyl)-amino]-2-(methylsulphinyl)-acetophenone with a melting point of 140° (slow decomposition) from methyl N-(o-dichlorophenyl)-anthranilate (melting point 103°–104°), (c) 2'-(N-methylamino)-5'-chloro-2-(methylsulphinyl)-acetophenone with a melting point of 131°–133° from methyl N-methyl-5-chloroanthranilate, and (d) 2'-[N-methyl-N-(m-trifluoromethylphenyl)-amino]-2-(methylsulphinyl)-acetophenone (oil, purified by chromatography) from methyl N-methyl-N-(m-trifluoromethylphenyl)-anthranilate (c.f. Example 2).

EXAMPLE 6

Under nitrogen, 9.1 g of a 55% strength dispersion of sodium hydride, which has been pre-washed with pentane, are suspended in 40 ml of dimethylsulphoxide. The suspension is warmed to 72°–73°. After the evolution of hydrogen has ceased, the mixture is cooled to 0°–5° and, at this temperature, a solution of 17 g of 5-(dimethylsulphamoyl)-isatoic anhydride in 80 ml of dimethylsulphoxide is added dropwise in the course of about 30 minutes. The mixture is stirred for 90 minutes at room temperature and is then poured into ice-water. After acidifying with 2 N hydrochloric acid, the mixture is extracted with methylene chloride. The methylene chloride extracts give 2'-amino-5'-(dimethylaminosulphamoyl)-2-(methylsulphinyl)-acetophenone, which is recrystallised from ethanol and has a melting point of 172°–173°.

EXAMPLE 7

5.3 g of a dispersion (55%) of sodium hydride are freed from mineral oil with pentane in the customary manner and 55 ml of dimethylsulphoxide are then added. The reaction mixture is stirred at 75° for 20 minutes and then cooled to room temperature and a solution of 14 g of methyl N-(2-methyl-3-chlorophenyl)-N-benzoyl-anthranilate (melting point 121°–122°) in 40 ml of tetrahydrofurane is then added in the course of 60 minutes at 0°–5°. The mixture is stirred for a further one hour at room temperature. The reaction solution is then poured into ice-water, the pH is adjusted to 4 with 1 N hydrochloric acid and the mixture is extracted three times with ethyl acetate. The organic phases are washed with icewater until neutral, dried, combined and evaporated. This gives 2'-[N-(2-methyl-3-chlorophenyl)-N-benzoyl-amino]-2-(methylsulphinyl)-acetophenone, which is dissolved in 260 ml of ethanol. 160 g of 4% strength sodium hydroxide solution are added to the solution and the mixture is kept under reflux for two hours. The alcohol is evaporated off from the reaction mixture. The pH of the aqueous solution is adjusted to 5 and the solution is extracted with methylene chloride. The organic phases are washed with sodium bicarbonate and water, dried over sodium sulphate and evaporated. The residue is recrystallised twice from methylene chloride/petroleum ether. This gives 2'-[N-(2-methyl-3-chlorophenyl)-amino]-2-(methylsulphinyl)-acetophenone with a melting point of 130°–132°.

EXAMPLE 8

Tablets containing 15 mg of active substance are prepared in the following composition in the customary manner,

| Composition | |
|---|---|
| 2'-[N-(m-trifluoromethylphenyl)-amino]-2-(methylsulphonyl)-acetophenone | 15.0 mg |
| wheat starch | 29.5 mg |
| lactose | 45.0 mg |
| colloidial silica | 5.0 mg |
| talc | 5.0 mg |
| magnesium stearate | 0.5 mg |
| | 100.0 mg |

Preparation

The 2'-[N-(m-trifluoromethylphenyl)-amino]-2-(methylsulphonyl)-acetophenone preparation is mixed with a portion of the wheat starch and with the lactose and colloidal silica and the mixture is forced through a sieve. A further portion of the wheat starch is mixed to a paste with 5 times the amount of water on a waterbath and the powder mixture is kneaded with this paste until a slightly plastic mass has formed.

The plastic mass is pressed through a sieve of about 3 mm mesh width and dried and the dry granules are again forced through a sieve. The remaining wheat starch, the talc and the magnesium stearate are then mixed in and the resulting mixture is pressed to give tablets weighing 100 mg with a cross-shaped groove.

We claim:

1. An ortho-aminoacetophenone of the formula I

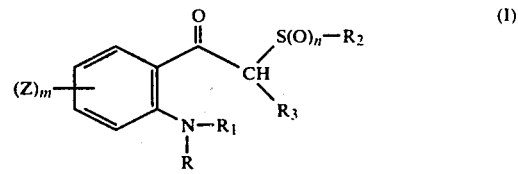

and its tautomers, in which Z is hydrogen, halogen, lower alkyl, cycloalkyl, lower alkoxy, trifluoromethyl, nitro or substituted or unsubstituted sulphamoyl, m is 1 or 2, R is aryl, $R_1$ is hydrogen or lower alkyl, $R_2$ is lower alkyl, cycloalkyl, aryl, cycloalkyl-lower alkyl, aryl-lower alkyl or substituted or unsubstituted pyridyl, $R_3$ is hydrogen or lower alkyl and n is 1 or 2, with the exception of 2'-[N-(p-methoxyphenyl)-amino]-2-(methyl-sulphinyl)-acetophenone, or its salts.

2. An ortho-aminoacetophenone Ib of the formula I according to claim 1, in which Z, m, R, $R_1$ and $R_2$ are as defined therein and $R_3$ is hydrogen or lower alkyl having 1–3 C atoms, with the exception of the compound mentioned by name in claim 1.

3. An ortho-aminoacetophenone Ic of the formula I according to claim 1, in which Z is hydrogen, halogen, lower alkyl, cycloalkyl, lower alkoxy, trifluoromethyl or substituted or unsubstituted sulphamoyl, m is 1, R is phenyl which is unsubstituted or polysubstituted or monosubstituted by lower alkyl, lower alkoxy, halogen or trifluoromethyl, $R_1$ is hydrogen or lower alkyl, $R_2$ is lower alkyl, phenyl which is unsubstituted or polysubstituted or monosubstituted by lower alkyl, lower alkoxy, halogen or trifluoromethyl, benzyl which is unsubstituted by polysubstituted or monosubstituted by lower alkyl, lower alkoxy, halogen or trifluoromethyl, or 2-pyridyl, 3-pyridyl or 4-pyridyl, n is 1 or 2 and $R_3$ is hydrogen or methyl, with the exception of the compound mentioned by name in claim 1.

4. An ortho-aminoacetophenone Id of the formula I according to claim 1, in which m is 1 and Z is hydrogen, lower alkyl, cyclopentyl, cyclohexyl, lower alkoxy, trifluoromethyl or substituted or unsubstituted sulphamoyl, R is phenyl which is unsubstituted or polysubstituted or monosubstituted by lower alkyl, lower alkoxy, halogen or trifluoromethyl, $R_1$ is hydrogen or α-unbranched lower alkyl, $R_2$ is lower alkyl, benzyl or phenyl which is unsubstituted or polysubstituted or monosubstituted by lower alkyl, lower alkoxy, halogen or trifluoromethyl, or pyridyl, n is 2 and $R_3$ is hydrogen, with the exception of the compound mentioned by name in claim 1.

5. An ortho-aminoacetophenone Ie of the formula I according to claim 1, in which m is 1 and Z is hydrogen, lower alkyl, cyclopentyl, cyclohexyl, lower alkoxy, trifluoromethyl or sulphamoyl, R is phenyl which is unsubstituted or polysubstituted or monosubstituted by lower alkyl, lower alkoxy, halogen or trifluoromethyl, $R_1$ is hydrogen, $R_2$ is lower alkyl, benzyl or phenyl which is unsubstituted or polysubstituted or monosubstituted by lower alkyl, lower alkoxy, halogen or trifluoromethyl, or 2-pyridyl, 3-pyridyl or 4-pyridyl, $R_3$ is hydrogen and n is 1 or 2, with the exception of the compound mentioned by name in claim 1.

6. An ortho-aminoacetophenone Ii of the formula I according to claim 1, in which m is 1 or 2, Z is halogen, lower alkyl, cycloalkyl, lower alkoxy, trifluoromethyl or di-lower alkyl-sulphamoyl, R is p-methoxyphenyl, $R_1$ is hydrogen, $R_2$ is methyl, $R_3$ is hydrogen and n is 1.

7. An ortho-aminoacetophenone Ij of the formula I according to claim 1, in which Z is hydrogen, halogen or di-lower alkylsulphamoyl, m is 1 or 2, R is phenyl, trifluoromethylphenyl, bis-trifluoromethylphenyl, lower alkylphenyl, di-lower alkylphenyl, halogenophenyl, dihalogenophenyl, or halogeno-lower alkylphenyl, $R_1$ is hydrogen or lower alkyl, $R_2$ is lower alkyl or phenyl, $R_3$ is hydrogen and n is 1 or 2, with the exception of the compound mentioned by name in claim 1.

8. An ortho-aminoacetophenone claimed in claim 1 in the racemic form or in the form of its antipodes.

9. An ortho-aminoacetophenone claimed in claim 1 in the form of a salt thereof.

10. An ortho-aminoacetophenone Ij of the formula I according to claim 1, in which Z is hydrogen, chlorine or dimethylsulphamoyl, m is 1, R is 3,5-bis-trifluoromethylphenyl, 3-trifluoromethylphenyl, 2,6-dichlorophenyl,2-methyl-3-chlorophenyl, or 2,3-dimethylphenyl, $R_1$ is hydrogen or methyl, $R_2$ is methyl or phenyl, $R_3$ is hydrogen and n is 1 or 2, with the exception of the compound mentioned by name in claim 1.

11. An ortho-aminoacetophenone according to claim 1 and being the 2'-[N-(m-trifluoromethylphenyl)-amino]-2-(methylsulphonyl)-acetophenone.

12. A fibrinolytic and antiinflammatory pharmaceutical formulation containing a correspondingly effective amount of an orthoaminoacetophenone as claimed in claim 1, together with a pharmaceutical, solid or liquid excipient.

13. A fibrinolythic and antiinflammatory pharmaceutical formulation containing a correspondingly effective amount of an ortho-aminoacetophenone of the formula I

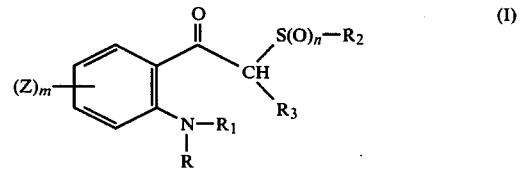

and its tautomers, in which Z is hydrogen, halogen, lower alkyl, cycloalkyl, lower alkoxy, trifluoromethyl, nitro or substituted or unsubstituted sulphamoyl, m is 1 or 2, R is lower alkyl, $R_1$ is hydrogen or lower alkyl, $R_2$ is lower alkyl, cycloalkyl, aryl, cycloalkyl-lower alkyl, aryl-lower alkyl or substituted or unsubstituted pyridyl, $R_3$ is hydrogen or lower alkyl and n is 1 or 2, or its salts, with the exception of 2'-methylamino-2-(methylsulphinyl)-acetophenone, together with a pharmaceutical, solid or liquid excipient.

* * * * *